(12) United States Patent
Frederick et al.

(10) Patent No.: US 9,615,973 B1
(45) Date of Patent: Apr. 11, 2017

(54) SURGICAL KNIFE

(71) Applicant: Surgical Specialties Corporation, Reading, PA (US)

(72) Inventors: Jeffrey Frederick, Reading, PA (US); Michael Barnett, Reading, PA (US)

(73) Assignee: SURGICAL SPECIALTIES CORPORATION, Braintree, MA (US)

( * ) Notice: Subject to any disclaimer, the term of this patent is extended or adjusted under 35 U.S.C. 154(b) by 290 days.

(21) Appl. No.: 13/892,270

(22) Filed: May 11, 2013

Related U.S. Application Data

(60) Provisional application No. 61/646,344, filed on May 13, 2012, provisional application No. 61/763,655, filed on Feb. 12, 2013.

(51) Int. Cl.
*B26B 9/00* (2006.01)
*B26B 5/00* (2006.01)
*A61F 9/013* (2006.01)

(52) U.S. Cl.
CPC .................................. *A61F 9/0133* (2013.01)

(58) Field of Classification Search
CPC ............... A61F 9/0133; A61F 9/00736; A61B 17/3211; A61B 5/1411
USPC .......... 30/353; 616/167, 161, 170, 171, 174, 616/232, 181, 166
See application file for complete search history.

(56) References Cited

U.S. PATENT DOCUMENTS

| | | | | |
|---|---|---|---|---|
| 7,465,310 B2 * | 12/2008 | Isogimi | ................. | A61F 9/0133 606/167 |
| 2003/0088258 A1 * | 5/2003 | Feaster | ................. | A61F 9/0133 606/166 |
| 2006/0100654 A1 * | 5/2006 | Fukuda | ................ | A61B 5/1411 606/181 |

\* cited by examiner

*Primary Examiner* — Ghassem Alie

(57) ABSTRACT

One or more wedges may be introduced into the bevel of a surgical knife near its tip, to thereby increase the bevel surface area of the knife, and thus increase the cutting edges of the knife, and render the knife more effective and/or easier to use in surgical applications such as ophthalmic procedures.

10 Claims, 5 Drawing Sheets

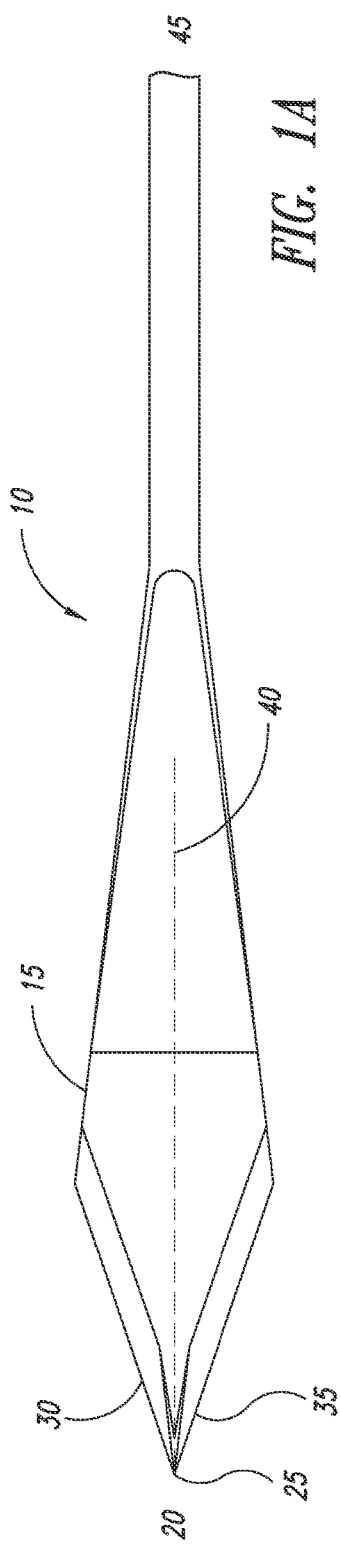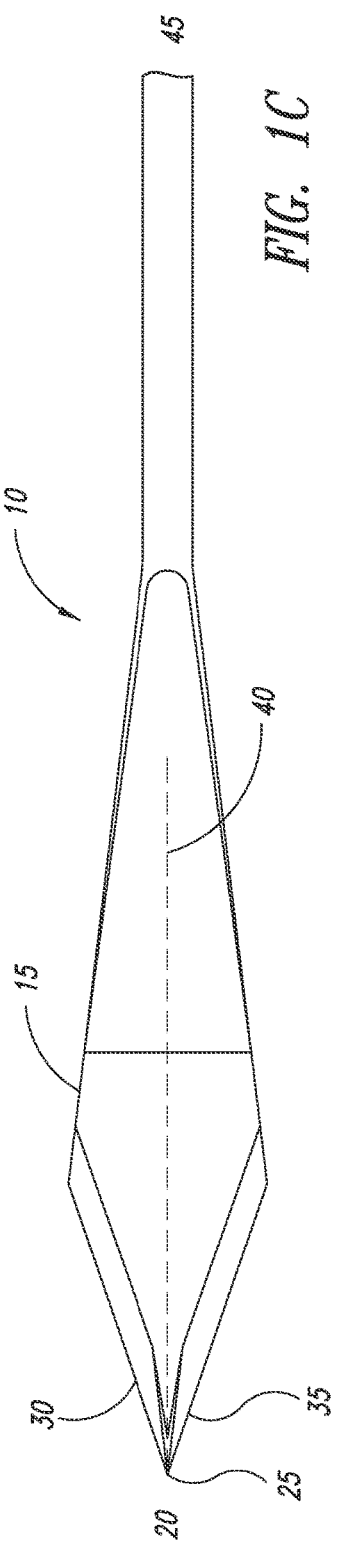

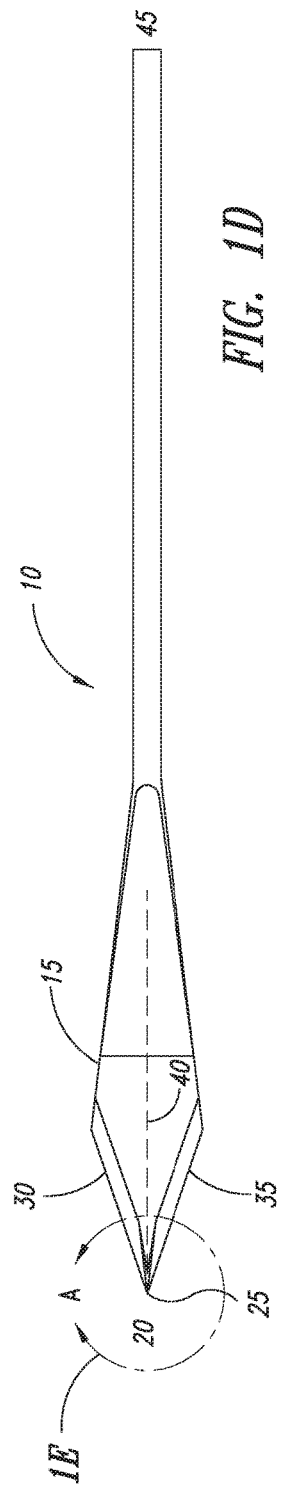
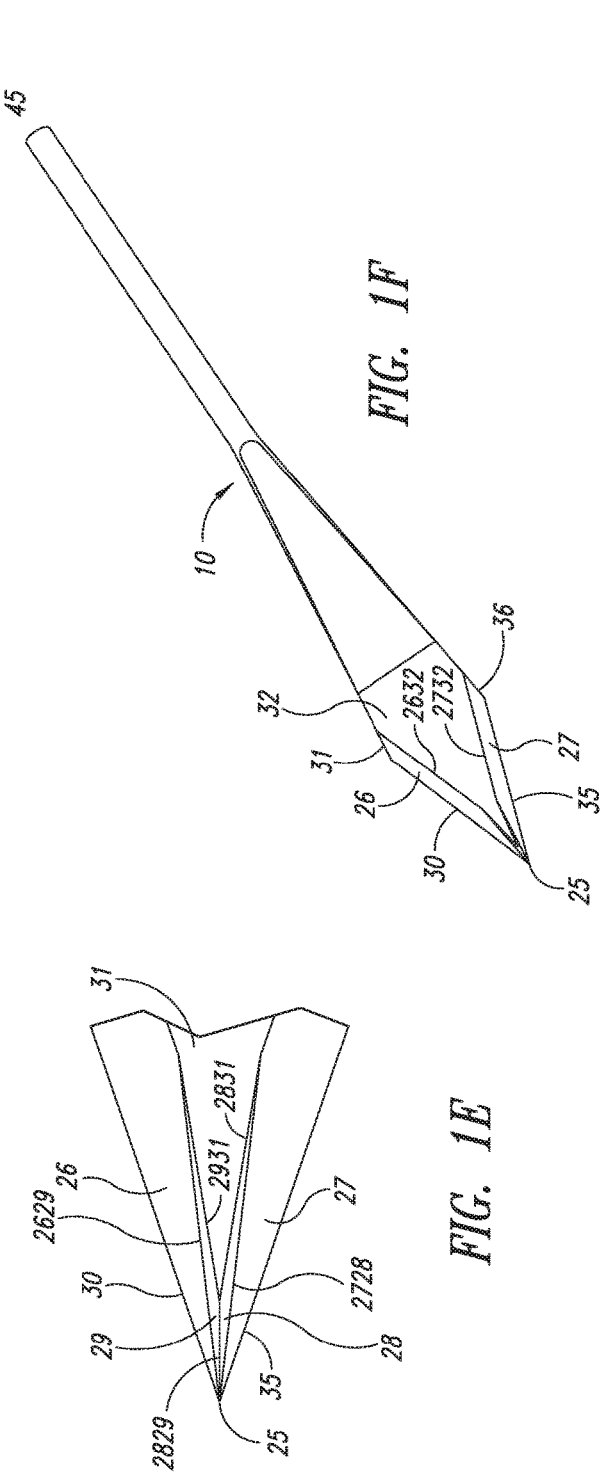

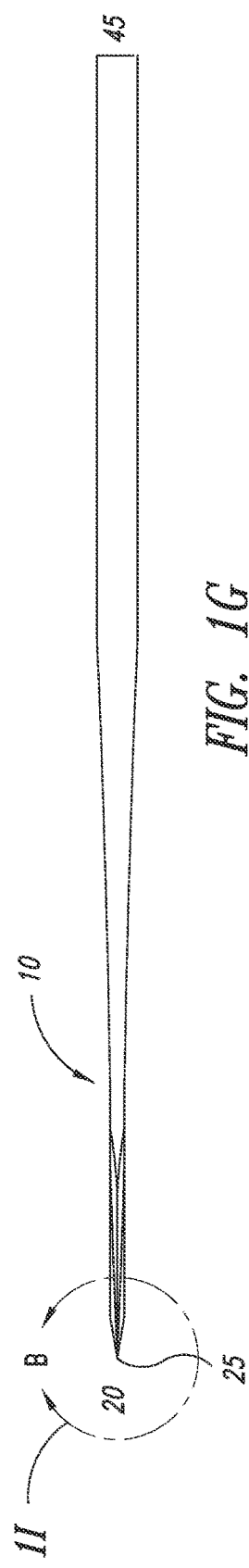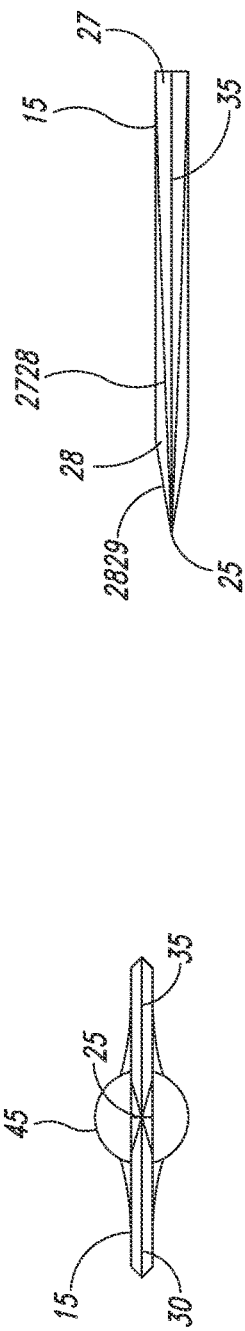
FIG. 1G
FIG. 1H
FIG. 1I

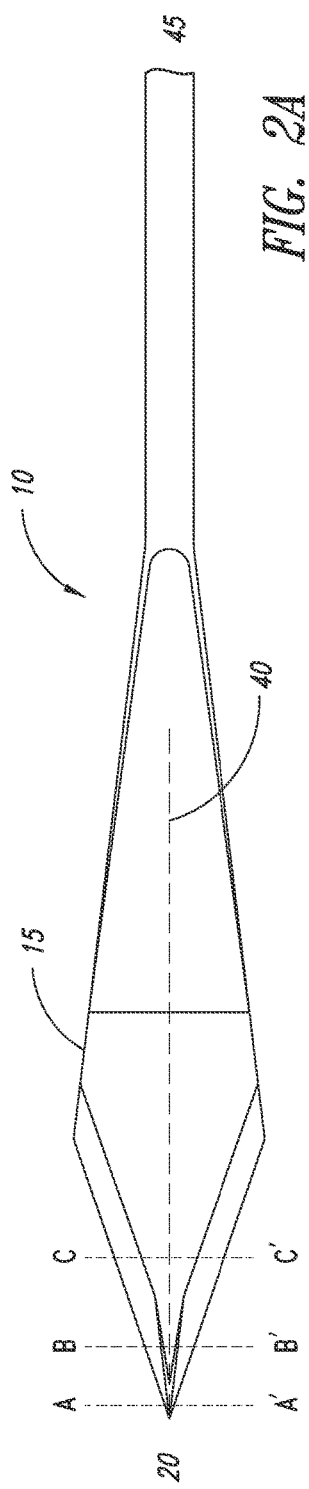
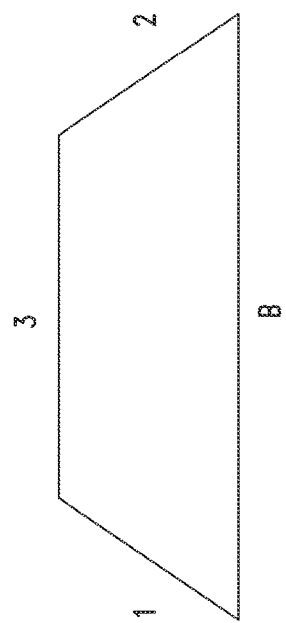
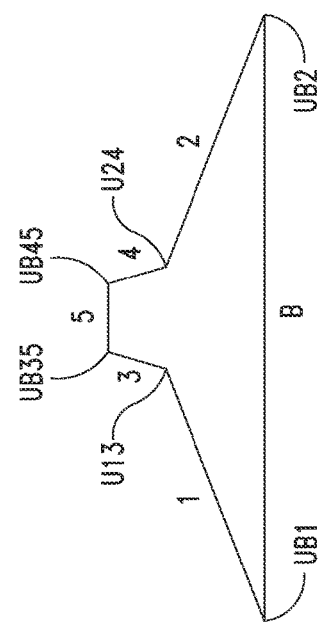
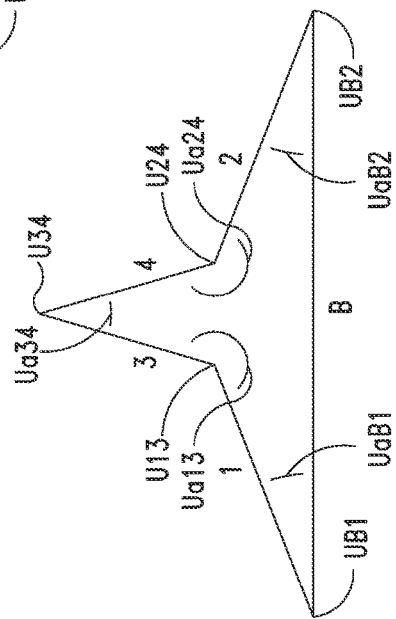

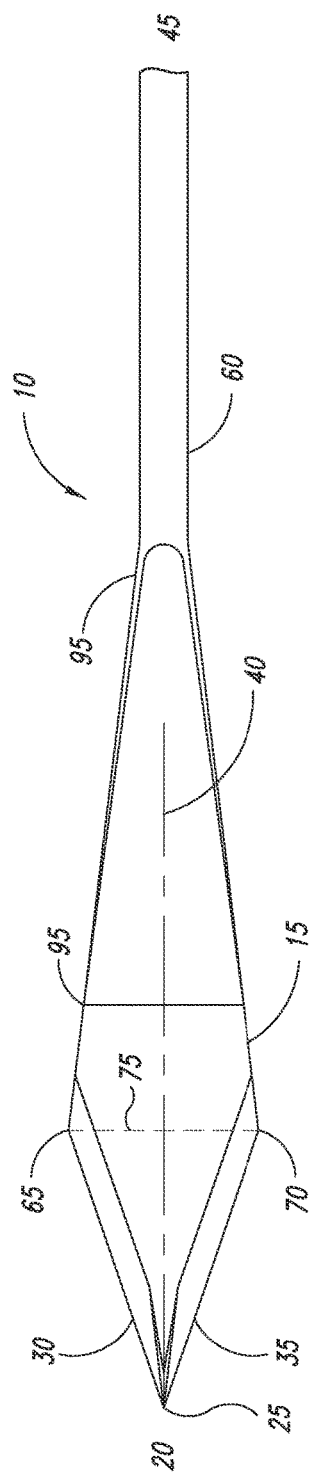
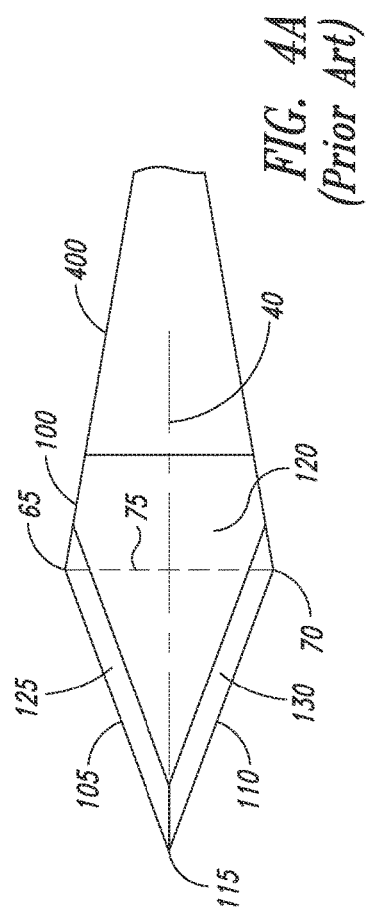
FIG. 3
FIG. 4A (Prior Art)
FIG. 4B

SURGICAL KNIFE

CROSS-REFERENCE TO RELATED APPLICATIONS

This application claims the benefit under 35 U.S.C. §119 (e) of U.S. Provisional Patent Application No. 61/646,344 filed May 13, 2012, and U.S. Provisional Patent Application No. 61/763,655, filed Feb. 12, 2013, which provisional applications are incorporated herein by reference in their entireties.

FIELD OF THE INVENTION

The present invention relates generally cutting instruments, the manufacture and use thereof, and in particular cutting instruments for surgical use, for example knives for ophthalmic surgery.

BACKGROUND

Knives for surgical procedures, including knives for ophthalmic and specialty surgery procedures have been described and many are available in the marketplace from various manufacturers. See, e.g., U.S. Pat. Nos. 4,898,170; 4,955,894; 6,139,559; 6,547,802; 6,554,840; 6,908,471; 7,465,310; 7,648,516; 8,080,027; D535,747. See also U.S. Patent Publication No. 2011/0092994.

SUMMARY

One or more wedges may be introduced into the bevel of a surgical knife to, in various embodiments, thereby increase the bevel surface area of the knife, the cutting edges of the knife, and render the knife more effective and/or easier to use. In one embodiment, the introduction of a wedge into the bevel of the knife will cause the cross-section of the blade to be in the form of a concave polygon.

In one aspect there is provided a knife blade having a cutting distal end, a non-cutting proximal end, two cutting edges disposed on either side of the cutting end, an upper blade surface having an upper periphery and a lower blade surface having a lower periphery, the two cutting edges each disposed in a single plane, the blade having a first cross-section including the two cutting edges, the first cross-section having an upper profile defined by a baseline lying in the plane and a plurality of line segments defined by the upper periphery of the upper blade surface, and a lower profile comprising the baseline, the upper profile being in a shape, the shape being characterized as a convex polygon. Optionally, the convex polygon has 5 sides and/or the convex polygon has two internal angles that are each greater than 180°.

Optionally, the baseline has first and second ends corresponding to the cutting edges, the first and second ends of the baseline being connected to first and second line segments at vertices UB1 and UB2 respectively, the first and second line segments each having an end not joined to the baseline where those ends are joined to ends of third and fourth line segments, respectively, at vertices U13 and U24, respectively, the third and fourth line segments each having an end not joined to either the third or fourth line segments where those two ends are joined to each other at vertex U34, where vertices UB1, UB2, U13, U24 and U34 may be defined as having inner angles UaB1, UaB2, Ua13, Ua24 and Ua34, respectively, where Ua13 and Ua24 are each greater than 180°. For example, UaB1 and UaB2 are each within the range of 5-15°.

Optionally, the blade has a second cross-section including the two cutting edges, the second cross-section having an upper profile defined by a baseline lying in the plane and a plurality of line segments defined by the upper periphery of the upper blade surface, and a lower profile comprising the baseline, the upper profile being in a shape, the shape being characterized as a convex polygon, the second cross-section being proximal to the first cross-section. For example, the upper profile of the first cross section is a pentagon and the upper profile of the second cross section is a hexagon.

Optionally, the blade may have a third cross-section including the two cutting edges, the third cross-section having an upper profile defined by a baseline lying in the plane and a plurality of line segments defined by the upper periphery of the upper blade surface, and a lower profile comprising the baseline, the upper profile being in a shape, the shape being characterized as a convex polygon, the third cross-section being proximal to the first and optionally second cross-section. The upper profile at the third cross section may be a convex polygon, e.g., a convex polygon having four sides.

Optionally, the blade may be characterized in terms of the first cross section only, the first and second cross sections only, the first and third cross sections only, or the first, second and third cross sections, each as described above and herein.

As for the lower profile of the knife blade, the lower profile may be the mirror image of the upper profile at each cross-section of the blade. Alternatively, the lower profile is only the baseline, in other words, the bottom of the blade is flat. As another alternative, the lower profile is a convex polygon at each cross section of the blade, e.g., a convex polygon having three sides.

The bevels of the cutting blade of the present disclosure may be described in terms of a plurality of planes. For example, in one aspect, the present invention provides a knife blade having a cutting distal end, a non-cutting proximal end, two cutting edges disposed on either side of the cutting end, an upper blade surface having an upper periphery and a lower blade surface having a lower periphery, the two cutting edges each disposed in a single plane. The knife blade comprises first, second, third and fourth planes that define, in part, the top periphery of the blade. The first and second planes have an identical number of sides selected from 3 and 4 to form a triangle or quadrangle shape, respectively, and the third and fourth planes have an identical number of sides selected from 3 and 4 to form a triangle or quadrangle shape, respectively. The first and third planes have a common side, the second and fourth planes have a common side, and the third and fourth planes have a common side. Such a knife is illustrated in the Figures and described in more detail hereafter. In various embodiment of this knife blade, any one or any two or any three or more of the following descriptions may be added: a side of the first plane and a side of the second plane are each a cutting edge of the blade, and these edges meet to form a point of the blade; the third and fourth planes have equal surface area; the first and second planes have equal surface area; the third and fourth planes each have a surface area smaller than either of the first and second planes; the first and third planes intersect along a line that is longer than the line along which the third and fourth planes intersect; the third and fourth planes each intersect, in part, a fifth plane; the first and second planes each intersect, in part, a sixth plane, where optionally the fifth and sixth planes are identical. The bottom periphery of the blade may be the same or different as the top periphery of the blade.

In another aspect, the present disclosure provides a knife blade comprising a surface, where the surface is formed, in part or whole, from a plurality of planes. The plurality of planes comprise a) a first plane comprising a first edge, the first edge providing a cutting edge for the blade; b) a second plane comprising a second edge, the second edge providing a cutting edge for the blade, where the first edge meets the second edge to form a point of the blade; and c) a third plane and a fourth plane, where the third plane intersects the first and fourth planes and the fourth plane intersects the second and third planes. In various embodiment of this knife blade, any one or any two or any three or more of the following descriptions may be added: the blade has a longitudinal axis running from the point of the blade through the center of the blade and towards a handle attached to the blade, the longitudinal axis dividing the blade into two sides, where the first plane is entirely on one side of the longitudinal axis and the second plane is entirely on the other side of the longitudinal axis; the plurality of planes includes a fifth plane, the fifth plane intersecting the third and fourth planes; the plurality of planes includes a fifth plane, where the fifth plane intersects the first and second planes.

In another aspect, the present disclosure provides a knife blade comprising a cutting distal end, a non-cutting proximal end, two cutting edges disposed on either side of the cutting end, the two cutting edges disposed in an imaginary plane, each cutting edge running from a tip of the blade to an ear of the blade, an outer cutting surface contiguous with each cutting edge, each outer cutting surface adjoining an inner cutting surface, each inner cutting surface running from the tip of the blade in a proximal direction for a distance which is less than the distance to an ear of the blade, an outer cutting surface forming a first angle relative to the imaginary plane and an inner cutting surface forming a second angle relative to the imaginary plane, where the first and second angles are non-identical. In optional embodiments, any two or more of which may be combined, the present disclosure additionally provides that: the blade comprises two inner cutting surfaces, where the two inner cutting surfaces adjoin one another for a distance; an inner cutting surface adjoins one but not two outer cutting surfaces; an inner cutting surface is a plane having three sides; an outer cutting surface is a plane having four sides, one of the four sides being a cutting edge; the blade is symmetrical across a central axis running from the tip of blade to the proximal end of the blade, i.e., the right and left sides of the blade look the same; a top side of the blade and a bottom side of the blade meet at the cutting edges, where the top and bottom sides are identical. As mentioned above, each inner cutting surface runs from the tip of the blade in a proximal direction for a distance which is less than the distance to an ear of the blade, where this direction is measured along a central axis, and may be up to 80%, or 70%, or 60%, or 50%, or 40%, or 35%, or 30%, or 25%, or up to 20% of the distance from the tip of the blade to a line that bisects the two ears of the knife. In contrast, each outer cutting surface runs for a distance which is at least 100% of the distance from the tip of the blade to a line that bisects the two ears of the knife.

Knives having such blades are provided, where the knives may have various handles and various intermediate structures that connect the handles to the knives. The knives may incorporate various safety features to reduce the likelihood that the health care provider using the knife will accidentally cut tissue. Methods of making the blades are described. The knives may be used in ophthalmic procedures where it is necessary to cut a portion of the eye, e.g., the cornea.

In various aspects, the present disclosure optionally provides one or more of the following numbered embodiments 1) A knife blade having a cutting distal end, a non-cutting proximal end, two cutting edges disposed on either side of the cutting end, an upper blade surface having an upper periphery and a lower blade surface having a lower periphery, the two cutting edges each disposed in a single plane, the blade having a first cross-section including the two cutting edges, the first cross-section having an upper profile defined by a baseline lying in the plane and a plurality of line segments defined by the upper periphery of the upper blade surface, and a lower profile comprising the baseline, the upper profile being in a shape, the shape being characterized as a convex polygon.

2) The blade of embodiment 1 wherein the convex polygon has 5 sides.

3) The blade of embodiment 1 wherein the convex polygon has two internal angles that are each greater than 180°.

4) The blade of any of embodiments 1-3 wherein the baseline has first and second ends corresponding to the cutting edges, the first and second ends of the baseline being connected to first and second line segments at vertices UB1 and UB2 respectively, the first and second line segments each having an end not joined to the baseline where those ends are joined to ends of third and fourth line segments, respectively, at vertices U13 and U24, respectively, the third and fourth line segments each having an end not joined to either the third or fourth line segments where those two ends are joined to each other at vertex U34, where vertices UB1, UB2, U13, U24 and U34 may be defined as having inner angles UaB1, UaB2, Ua13, Ua24 and Ua34, respectively, where Ua13 and Ua24 are each greater than 180°.

5) The blade of embodiment 4 wherein UaB1 and UaB2 are each within the range of 5-15°.

6) The blade of any of embodiments 1-5 having a second cross-section including the two cutting edges, the second cross-section having an upper profile defined by a baseline lying in the plane and a plurality of line segments defined by the upper periphery of the upper blade surface, and a lower profile comprising the baseline, the upper profile being in a shape, the shape being characterized as a convex polygon, the second cross-section being proximal to the first cross-section.

7) The blade of embodiment 6 wherein the upper profile of the first cross section is a pentagon and the upper profile of the second cross section is a hexagon.

8) The blade of any of embodiments 1-7 having a third cross-section including the two cutting edges, the third cross-section having an upper profile defined by a baseline lying in the plane and a plurality of line segments defined by the upper periphery of the upper blade surface, and a lower profile comprising the baseline, the upper profile being in a shape, the shape being characterized as a convex polygon, the third cross-section being proximal to the first and optionally second cross-section.

9) The blade of embodiment 8 wherein the upper profile at the third cross section is a convex polygon.

10) The blade of embodiment 9 wherein the convex polygon has four sides.

11) The blade of embodiments 1-10 wherein the lower profile is the mirror image of the upper profile at each cross-section of the blade.

12) The blade of embodiments 1-10 wherein the lower profile is only the baseline, in other words, the bottom of the blade is flat.

13) The blade of embodiments 1-10 wherein the lower profile is a convex polygon at each cross section of the blade.

14) The blade of embodiment 13 wherein the convex polygon has three sides.

15) A knife blade having a cutting distal end, a non-cutting proximal end, two cutting edges disposed on either side of the cutting end, an upper blade surface having an upper periphery and a lower blade surface having a lower periphery, the two cutting edges each disposed in a single plane, the knife blade comprising first, second, third and fourth planes that define, in part, the periphery of the blade, where the first and second planes have an identical number of sides selected from 3 and 4 to form a triangle or quadrangle shape, respectively, and the third and fourth planes have an identical number of sides selected from 3 and 4 to form a triangle or quadrangle shape, respectively, where the first and third planes have a common side, the second and fourth planes have a common side, and the third and fourth planes have a common side.

16) The knife blade of embodiment 15 wherein a side of the first plane and a side of the second plane are each a cutting edge of the blade, and these edges meet to form a point of the blade.

17) The knife blade of embodiment 15 wherein the third and fourth planes have equal surface area.

18) The knife blade of embodiment 15 wherein the first and second planes have equal surface area.

19) The knife blade of embodiment 15 wherein the third and fourth planes each have a surface area smaller than either of the first and second planes.

20) The knife blade of embodiment 15 wherein the first and third planes intersect along a line that is longer than the line along which the third and fourth planes intersect.

21) The knife blade of embodiment 15 wherein the third and fourth planes each intersect, in part, a fifth plane.

22) The knife blade of embodiment 15 wherein the first and second planes each intersect, in part, a sixth plane 23) The knife blade of embodiment 22 wherein the fifth and sixth planes are identical.

24) A knife blade comprising a surface, the surface formed in part from a plurality of planes, the plurality of planes comprising a. a first plane comprising a first edge, the first edge providing a cutting edge for the blade;

b. a second plane comprising a second edge, the second edge providing a cutting edge for the blade, where the first edge meets the second edge to form a point of the blade;

c. a third plane and a fourth plane, where the third plane intersects the first and fourth planes and the fourth plane intersects the second and third planes.

25) The knife blade of embodiment 24 having a longitudinal axis running from the point of the blade through a center of the blade and towards a handle attached to the blade, the longitudinal axis dividing the blade into two sides, where the first plane is entirely on one side of the longitudinal axis and the second plane is entirely on the other side of the longitudinal axis.

26) The knife blade of embodiment 24, further comprising a fifth plane, the fifth plane intersecting the third and fourth planes.

27) The knife blade of embodiment 24 further comprising a fifth plane, the fifth plane intersecting the first and second planes.

28) A knife blade comprising a cutting distal end, a non-cutting proximal end, two cutting edges disposed on either side of the cutting end, the two cutting edges disposed in an imaginary plane, each cutting edge running from a tip of the blade to an ear of the blade, an outer cutting surface contiguous with each cutting edge, each outer cutting surface adjoining an inner cutting surface, each inner cutting surface running from the tip of the blade in a proximal direction for a distance which is less than the distance to an ear of the blade, an outer cutting surface forming a first angle relative to the imaginary plane and an inner cutting surface forming a second angle relative to the imaginary plane, where the first and second angles are non-identical.

29) The blade of embodiment 28 comprising two inner cutting surfaces, where the two inner cutting surfaces adjoin one another for a distance.

30) The blade of embodiment 29 wherein an inner cutting surface adjoins one but not two outer cutting surfaces.

31) The blade of embodiment 28 wherein an inner cutting surface is a plane having three sides.

32) The blade of embodiment 28 wherein an outer cutting surface is a plane having four sides, one of the four sides being a cutting edge.

33) The blade of embodiment 28 which is symmetrical across a central axis running from the tip of blade to the proximal end of the blade.

34) The blade of embodiment 28 wherein a top side of the blade and a bottom side of the blade meet at the cutting edges, where the top and bottom sides are identical.

35) The blade of embodiment 28 wherein each inner cutting surface runs from the tip of the blade in a proximal direction along a longitudinal axis for a distance which is less than 60% of the distance from the tip of the blade to a line which bisects the ears of the blade.

The details of one or more embodiments are set forth in the description below. The features illustrated or described in connection with one exemplary embodiment may be combined with the features of other embodiments. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the present disclosure, its nature and various advantages will be apparent from the accompanying drawings and the following detailed description of various embodiments. Corresponding reference numerals indicate corresponding parts throughout the drawings.

FIG. 1A is a planar view of a knife, viewing the top surface of the knife.

FIG. 1B is a side view of the knife of FIG. 1A, viewing the edge of the knife.

FIG. 1C is a planar view of the knife of FIG. 1A, viewing the bottom surface of the knife.

FIG. 1D replicates FIG. 1A but additionally identifies a region encircled by circle "B" that is shown in expanded view in FIG. 1E.

FIG. 1E is a planar view of a proximal portion of the knife of FIG. 1A, showing an expanded view of the cutting portion of the knife.

FIG. 1F is a perspective view of the knife of FIG. 1A.

FIG. 1G replicates FIG. 1B but additionally identifies a region encircled by circle "A" that is shown in expanded view in FIG. 1H and FIG. 1I.

FIG. 1H illustrates a knife of the present disclosure in expanded view, looking along the longitudinal axis of the knife towards the tip, or point, of the knife.

FIG. 1I illustrates a knife of the present disclosure in expanded view, looking from the side of the knife at the proximal or cutting end of the blade.

FIG. 2A is a planar view of a knife, viewing what may be either the top surface or the bottom surface of a knife of the present disclosure, and showing three locations (A-A; B-B; and C-C') where cross-sections through the longitudinal axis of the knife may be taken.

FIG. 2B is a cross-sectional view of the knife of FIG. 2A taken at location A-A', and viewing along the longitudinal axis of the knife, illustrating that the cross section at location A-A' is in the form of a concave polygon.

FIG. 2C is a cross-sectional view of the knife of FIG. 2A taken at location B-B', and viewing along the longitudinal axis of the knife, illustrating that the cross section at location B-B' is in the form of a concave polygon which is different from the concave polygon shown in FIG. 2B.

FIG. 2D is a cross-sectional view of the knife of FIG. 2A taken at location C-C', and viewing along the longitudinal axis of the knife, illustrating that the cross section at location C-C' is in the form of a convex polygon.

FIG. 3 is a planar view of a knife of the present disclosure.

FIG. 4A is a planar view showing the top side of a prior art blade.

FIG. 4B is a planar view showing the top side of a knife disclosed herein.

DETAILED DESCRIPTION OF THE INVENTION

The present disclosure provides a blade for a surgical knife, a surgical knife incorporating the blade, a method of manufacturing the blade, a method of manufacturing the knife, and a method of using the knife in a surgical procedure.

A popular knife for ophthalmic and specialty surgical applications is the slit knife, which includes what is commonly called a slit blade. Such a blade is shown in FIG. 4A. This blade has sharp point 115 for making an initial incision, and then cutting edges 105, 110 that run from the point 115 to the ears 65 and 75, respectively, of the blade. The cutting edges 105, 110 are continuous with a cutting surface 125, 130, respectively, where the plane of a cutting surface 125 or 130 forms an angle with an imaginary plane wherein lies the cutting edges 105 and 110, and also forms an angle with the center region 120 of the blade. Such a blade is often described as having a bevel, the bevel running between the cutting edge 105, 110 and the center region 120 of the blade. The cutting surfaces 125 and 130 are said to run upwards from the cutting edges 105, 110, respectively, and accordingly a blade of this design is sometimes said to have a bevel up design.

The slit blade design is very popular among ophthalmic surgeons. In order to have a very sharp cutting edge on a slit blade, it is typically desirable that the blade be quite thin. However, as a blade becomes thinner, it also becomes less sturdy and more prone to bend under pressure. This problem is particularly evident at the point 115 of the blade. As the blade becomes thinner, the region of the blade at and near the point 115 more easily bends under pressure, which is highly undesirable from the surgeon and patient's point of view. The blade and knives of the present invention address this problem.

The blades and knives of the present disclosure have a traditional slit blade design running from the ears of the blade for some distance towards the point of the blade. However, near its point, the blades and knives of the present disclosure introduce a second bevel which adds strength to the tip region of the blade while introducing little additional thickness. Accordingly, the blades and knives of the present disclosure can be made with a thinness, and accordingly provide an enhanced sharpness, over much of the cutting edge surface to a degree that, absent the second bevel, would provide a knife with unacceptably low rigidness near the tip. Stated another way, the blades and knives of the present disclosure incorporate a second cutting surface in the region of the tip, where this second cutting surface adds mass and hence strength to this tip region. The blades and knives of the present disclosure have a single cutting surface extending along the cutting edge from the ears and for some distance (to point "x") from the ears, and then have two or more, preferably two cutting surfaces which extend from the tip to the point "x" along the cutting edge.

In other words, the blades and knives of the present disclosure have an outer cutting surface which runs from the point 115 for a distance reaching an ear 65 or 70 along the cutting edge, and also have an inner cutting surface which runs from the point 115 for a distance that is less than the distance to an ear 65 or 70. The outer cutting surface is in the form a plane having a first angle with respect an imaginary plane that encompasses the two cutting edges of the blade, and the inner cutting surface is in the form of a plane having a second angle with respect to the imaginary plane that encompasses the two cutting edges, where the first and second angles are non-identical. An outer cutting surface is contiguous with an adjacent cutting edge between the tip and an ear, while an inner cutting surfaced is contiguous with the outer cutting surface between the tip and a distance which is less than the distance to the ear. The outer cutting surface will therefore abut or adjoin the inner cutting surface for a distance, and will abut or adjoin the center region for a distance.

Having now provided a general overview of a preferred embodiment of a knife and blade of the present disclosure, the knife and blade of the present disclosure will now be described in more detail by reference to the accompanying figures.

The blade of the present disclosure has a top and a bottom surface. An exemplary top surface is shown in FIG. 1A. The bottom surface may look identical to the top surface, or it may be non-identical. For example, while the top surface may have the appearance shown in FIG. 1A, the bottom surface may be flat, i.e., the entire bottom surface may lie within a single plane. As another example, while the top surface may have the appearance shown in FIG. 1A, the bottom surface may be non-planar, for example, curved in a slightly convex or concave manner. The following description which is directed to the top surface of the knife is equally applicable to the shape and appearance of the bottom surface of the knife. However, the top surface as described in the following description is not necessarily the same as the bottom surface of the knife.

An embodiment of the knife blade of the present disclosure is shown in FIG. 1A. As seen looking down onto the top of the knife 10 having a blade 15, the distal end 20 of the blade comes to a point 25. The blade comprises two cutting edges 30 and 35 adjacent to the distal point 25 of the blade 15 where each of those two cutting edges 30 and 35 is, at least in the vicinity of the distal end, in the form of a straight line. Those two straight lines intersect at the distal end 20 of the blade, and the point of the intersection is the "point" 25 of the knife. In this embodiment those two cutting edges 30 and 35 and the point 25 define an angle which is less than 180°, and in various aspects is less than 150°, is less than 120°, is less than 100°, is less than 90°, is less than 80°, is less than 70°, is less than 60°, is less than 55°, is less than 50°, less than 45°, is less than 40°, is less than 35°, is less than 30°, is less than 25°, is less than 20°, where this angle may also, optionally or alternatively, be characterized in terms of a minimum size, and in various aspects is greater than 15°, is greater than 20°, is greater than 25°, is greater than 30°, is greater than 35°, is greater than 40°, is greater than 45°, is greater than 50°, is greater than 55°, is greater than 60°, is greater than 70°, is greater than 80°, is greater than 90°, is greater than 100°, is greater than 120°, is greater than 140°. Any listed maximum angle may be combined with any listed minimum angle to provide a range of angles for a blade as described herein. For instance, and in specific aspects, the angle between the two cutting edges 30 and 35 may be from 20-60°, or from 30-50°, or from 35-45°.

In the embodiment illustrated in FIG. 1A, as seen looking down onto the knife, there are two cutting edges 30 and 35 adjacent to the point 25 of the blade 15 where both of those two cutting edges are, at least in the vicinity of the distal end, in the form of a straight line. Alternatively, the two cutting edges adjacent to the distal end of the blade need not be straight. For example, both of the cutting edges may be curved, or one of the cutting edges may be curved and the other cutting edge may be straight.

As viewed from the vantage point of looking down onto the top of the knife 10, the blade 15 will have two cutting edges 30 and 35, one cutting edge on either side of the point 25 of the blade. Each of those two cutting edges 30 and 35 begins at the distal end 20 of the blade 15, and terminates at a point or region some distance from the distal end of the blade, i.e., at some point or region nearer to the proximal end of the knife. The distance along a cutting edge between the distal point 25 of the blade and the location where the cutting edge terminates, will be referred to herein as the length of a cutting edge. As mentioned above, the shape of a cutting edge in the region of the blade nearest to the distal end of the blade may be straight or curved, where each of the cutting edges is independently straight or curved in its respective region. Along the entire length of a cutting edge, the shape of the cutting edge may retain its shape as present nearest the distal end of the blade. For example, a cutting edge may be curved along its entire length. Alternatively, the cutting edge may be straight along its entire length.

However, a cutting edge need not have the same shape along its entire length, and the shape of one cutting edge need not be the same as the shape of the other cutting edge. For instance, a cutting edge may follow a straight line from the distal point 25 of the knife to a proximal point A, where this line forms an angle X with the longitudinal axis 40 of the knife, and thereafter the cutting edge forms a straight line between proximal point A and a more proximal point B (point B being more distant from the distal end of the knife blade than is point A, as distance is measured along the length of the cutting edge) which, relative to the longitudinal axis of the knife, forms an angle Y. The angle X has been described elsewhere herein. The angle Y may be, for example, 90°, i.e., the cutting edge is disposed perpendicular to the longitudinal axis 40 and moving away from that axis in the direction from point A to point B, 0°, i.e., the cutting edge runs parallel to the longitudinal axis between the points A and B, or −90°, i.e., that cutting edge may travel in a direction directly toward the longitudinal axis from point A to point B, or the angle Y may be any angle there between. Likewise for the shape of the cutting edge between point B and a yet more proximal point C (point C being more distant from the distal end of the blade, as measured along the cutting edge, than is point B). Furthermore, in any region between the distal end of the blade and point A, or between point A and a point B, or between a point B and point C, etc., the shape of the cutting edge may be curved rather than straight, where the shape of the cutting edge is independently selected in each region.

As illustrated in FIG. 1A, the knife 10 may be described as having a cutting distal end 20, a non-cutting proximal end 45, two cutting edges 30 and 35 disposed on either side of the point of the knife 25, an upper blade surface 50 shown in FIG. 1B having an upper periphery and a lower blade surface 55 also shown in FIG. 1B having a lower periphery. The two cutting edges 30 and 35 are each disposed in a single imaginary plane, also called a reference plane. FIG. 1C shows one embodiment of a bottom side of a knife that is also shown in FIGS. 1A-1B and 1D-1I, where the top side as seen in FIG. 1A and the bottom side as seen in FIG. 1C are identical.

FIG. 1D shows the knife 10 that is also shown in FIG. 1A, but in FIG. 1D a region of the distal end of the knife is encircled by the line denoted "A", and this encircled region is shown in enlarged scale in FIG. 1E. In FIG. 1E, the point 25 of the blade 15 is located at the meeting of the cutting edge 30 and the cutting edge 35. Also shown in FIG. 1E are four planes that converge at the point 25. Those planes include a first plane 26 and a second plane 27. One side of the first plane 26 terminates at a first edge 30 which is a cutting edge for the blade, while one side of the second plane 27 terminates at a second edge 35 which is also a cutting edge for the blade. Each of the planes 26 and 27 may also be referred to as outer cutting surfaces. Disposed between the first and second planes are a third plane 28 and a fourth plane 29. The third and fourth planes each provide an inner cutting surface. The first plane 26 intersects with the fourth plane 29 along the line 2629 while the third plane 28 intersects with the second plane 27 along the line 2728. One side of the inner cutting surface 28 is continuous for a distance with one side of the outer cutting surface 27. In addition, the fourth plane 29 and the third plane 28 intersect with each other along the line 2829.

Thus, in one aspect, the present invention provides a knife blade comprising a surface, the surface formed in part from a plurality of planes. The plurality of planes comprise a first plane comprising a first edge, the first edge providing a cutting edge for the blade; a second plane comprising a second edge, the second edge providing a cutting edge for the blade, where the first edge meets the second edge to form a point of the blade. In addition, the plurality of planes comprises a third plane and a fourth plane, where the third plane intersects the first and fourth planes and the fourth plane intersects the second and third planes.

The knife blade illustrated by the encircled portion of FIG. 1D, and accordingly the portion of the blade shown in FIG. 1E, has a longitudinal axis 40 running from the point of the blade 25 through the center of the blade and towards a handle attached to the blade. In one embodiment, the longitudinal axis essentially divides the blade into two sides, where the first plane 28 is entirely on one side of the longitudinal axis 40 and the second plane 27 is entirely on the other side of the longitudinal axis 40.

The two planes 28 and 29 may, although need not, be separated by a plane 31 as shown in FIG. 1E. The plane 31, when present, intersects both of planes 28 and 29 along lines 2831 and 2931, respectively.

FIG. 1F shows the blade of FIG. 1A in perspective view. In FIG. 1F, a plane 32 is shown separating, and intersecting with, the planes 26 and 27, the intersection occurring along lines 2632 and 2732, respectively. This plane 32 may, although need not, separate planes 26 and 27. Optionally, the plane 32 shown in FIG. 1F and the plane 31 shown in FIG. 1E may be one and the same plane.

The two planes 26 and 27 may, although need not, be separated by a plane 31 as shown in FIG. 1E. The plane 31, when present, intersects each of planes 26 and 27.

The planes 28 and 29 intersect along the line 2829, where this line may be in the form a ridge. In other words, as viewed starting from the cutting edge 35, and traveling in a direction perpendicular to the longitudinal axis 40, the plane 27 rises as one moves from the edge 35 directly towards the longitudinal axis 40 until the plane 27 stops upon its intersection with plane 28 along line 2728. Continuing towards the longitudinal axis 40, and along a line perpendicular to the longitudinal axis 40, a line along the plane 28 continues to rise as one moves from the line 2728 towards the intersection of the plane 28 with the plane 29 which occurs along line 2829. Optionally, the line 2829 may lie in and along the longitudinal axis 40. Optionally, the slope at which the line rises along plane 27 may be less than the slope at which the line rises as it traverses plane 28, where the slope is referenced to a plane ("the reference plane") which contains both of cutting edges 30 and 35. Continuing on this straight line which is perpendicular to axis 40, and traveling along the plane 29, the line drops (i.e., moves towards the references plane, rather than rising, i.e., moving away from the reference plane) as it moves on plane 29 towards the cutting edge 30 and away from the cutting edge 35. After intersection of plane 29 with plane 26 at line 2629, the line crosses the line 2629 and then continues to drop as it traverses plane 26 until it reaches the cutting edge 30. Bearing in mind this description, it can be understood that the line 2829 forms a high point, or a ridge, relative to the reference plane, for a line which traverses line 2829 and runs perpendicular to the axis 40.

As shown in the blade embodiment illustrated in FIG. 1E, the planes 28 and 29 of the blade 15 may each have three sides or edges. In FIG. 1E, the plane 28 is shown to have one edge where plane 28 intersects with plane 27, i.e., one edge of plane 28 is the line 2728. In FIG. 1E, the plane 28 is shown to have one edge where plane 28 intersects with plane 29, i.e., one edge of plane 28 is the line 2829. In FIG. 1E, the plane 28 is shown to have one edge where plane 28 intersects with plane 31, i.e., one edge of plane 28 is the line 2831. Thus, in one embodiment, the plane 28 is three-sided, e.g., it is defined by the lines 2728, 2829, and 2831. Likewise, in one embodiment, the plane 29 is three-sided, e.g., it is defined by the lines 2629, 2829, and 2931.

As shown in the blade embodiments illustrated in FIG. 1F, the planes 26 and 27 of the blade 15 may each have four sides or edges. In FIG. 1F, the plane 26 has an edge 30 and an adjacent (intersecting) edge 31 which is proximal to the edge 30. Edge 31 is adjacent to (intersects with) the line formed by the intersection of planes 26 and plane 32, that is, line 2632 in FIG. 1F. The fourth edge of plane 26 is best seen by reference to FIG. 1E, where this fourth edge is formed upon the intersection of plane 26 with plane 29, i.e., the fourth edge is the line 2629. Likewise, in one embodiment, the plane 27 is four sided, e.g., it is defined by the cutting edge 35 (see FIGS. 1E and 1F), the edge 36 (see FIG. 1F), the intersection of plane 27 with plane 32 along line 2732 (see FIG. 1F) and the intersection of plane 27 with plane 28 along line 2728 (see FIG. 1E).

FIG. 1G essentially replicates FIG. 1B in showing a side view of the knife of FIGS. 1A-1I. In FIG. 1G, a portion of the distal region 20 of the blade 15 is encircled by the area B, where this encircled region is shown in expanded form in FIG. 1H and FIG. 1I. FIG. 1H shows a view of the knife looking directly towards the tip 25 along the longitudinal axis 40 and in the reference plane (also referred to herein as an imaginary plane) defined by cutting edges 30 and 35. The knife is seen as being symmetrical across the reference plane, in other words, the top and bottom of the knife are identical. FIG. 1I shows an expanded view of the side of the distal end 20 of the blade 15, including the tip 25, an inner cutting surface 28 and an outer cutting surface 27 of the topside of the knife, the topside being defined as that portion of the knife above the cutting edge 35, and also showing the intersection line 2728 where inner cutting surface 28 and outer cutting surface 27 adjoin. As discussed elsewhere herein, this line 2728 begins at the tip 25 but does not extend to the ears of the knife. Thus, the line 2728 is shorter than the cutting edge 35, where in various embodiments the line 2728 is less than 80%, 70%, 60%, 50%, 40%, 35%, 30%, 25%, or less than 20% of the distance of the cutting edge 35 which travels from the point 25 to an ear of the knife 70. By virtue of having line 2728 be shorter than cutting edge 35, the knife of the present disclosure has a slit blade design in the region of the ear of the knife, but does not a classical slit blade design in the region of the tip of the knife.

In one embodiment, the present disclosure provides a knife blade, the blade comprising first, second, third and fourth planes that define, in part, the surface of the blade, where the first and second planes are quadrangles, i.e., four sided, and the third and fourth planes are triangles, i.e., three sided. The first and third planes share a side, and the second and fourth planes share a side, and the third and fourth planes share a side. Optionally a side of the first plane and a side of the second plane are each a cutting edge of the blade, and these edges meet to form a point of the blade. Optionally, the third and fourth planes have equal surface area. Optionally, the first and second planes have equal surface area. Optionally, the third and fourth planes each have a surface area smaller than either of the first and second planes. Optionally, the first and third planes intersect along a line that is longer than the line along which the third and fourth planes intersect. Optionally, the third and fourth planes each intersect, in part, a fifth plane. Optionally, the first and second planes each intersect, in part, a sixth plane, where in one embodiment the fifth and sixth planes are the same plane.

In one embodiment, the present disclosure provides a knife blade, the blade comprising first, second, third and fourth planes that define, in part, the surface of the blade, where the first and second planes are quadrangles, i.e., four sided, and the third and fourth planes are quadrangles, i.e., four sided. The first and third planes share a side, and the second and fourth planes share a side, and the third and fourth planes share a side. Optionally a side of the first plane and a side of the second plane are each a cutting edge of the blade, and these edges meet to form a point of the blade. Optionally, the third and fourth planes have equal surface area. Optionally, the first and second planes have equal surface area. Optionally, the third and fourth planes each have a surface area smaller than either of the first and second planes. Optionally, the first and third planes intersect along a line that is longer than the line along which the third and fourth planes intersect. Optionally, the third and fourth planes each intersect, in part, a fifth plane. Optionally, the first and second planes each intersect, in part, a sixth plane, where in one embodiment the fifth and sixth planes are the same plane.

In one embodiment, the present disclosure provides a knife blade, the blade comprising first, second, third and fourth planes that define, in part, the surface of the blade, where the first and second planes are triangles, i.e., three sided, and the third and fourth planes are triangles, i.e., three sided. The first and third planes share a side, and the second and fourth planes share a side, and the third and fourth planes share a side. Optionally a side of the first plane and a side of the second plane are each a cutting edge of the blade, and these edges meet to form a point of the blade. Optionally, the third and fourth planes have equal surface area. Optionally, the first and second planes have equal surface area. Optionally, the third and fourth planes each have a surface area smaller than either of the first and second planes. Optionally, the first and third planes intersect along a line that is longer than the line along which the third and fourth planes intersect. Optionally, the third and fourth planes each intersect, in part, a fifth plane. Optionally, the first and second planes each intersect, in part, a sixth plane, where in one embodiment the fifth and sixth planes are the same plane.

In one embodiment, the present disclosure provides a knife blade, the blade comprising first, second, third and fourth planes that define, in part, the surface of the blade, where the first and second planes are triangles, i.e., three sided, and the third and fourth planes are triangles, i.e., three sided. The first and third planes share a side, and the second and fourth planes share a side, and the third and fourth planes share a side. Optionally a side of the first plane and a side of the second plane are each a cutting edge of the blade, and these edges meet to form a point of the blade. Optionally, the third and fourth planes have equal surface area. Optionally, the first and second planes have equal surface area. Optionally, the third and fourth planes each have a surface area smaller than either of the first and second planes. Optionally, the first and third planes intersect along a line that is longer than the line along which the third and fourth planes intersect. Optionally, the third and fourth planes each intersect, in part, a fifth plane. Optionally, the first and second planes each intersect, in part, a sixth plane, where in one embodiment the fifth and sixth planes are the same plane.

In one embodiment, the present disclosure provides a knife blade, the blade comprising first, second, third and fourth planes that define, in part, the surface of the blade, where the first and second planes are each selected from quadrangles and triangles, i.e., both of the first and second planes are either triangles or quadrangles, and the third and fourth planes are each selected from quadrangles and triangles, i.e., both of the third and fourth planes are either triangles or quadrangles. The first and third planes share a side, and the second and fourth planes share a side, and the third and fourth planes share a side. Optionally a side of the first plane and a side of the second plane are each a cutting edge of the blade, and these edges meet to form a point of the blade. Optionally, the third and fourth planes have equal surface area. Optionally, the first and second planes have equal surface area. Optionally, the third and fourth planes each have a surface area smaller than either of the first and second planes. Optionally, the first and third planes intersect along a line that is longer than the line along which the third and fourth planes intersect. Optionally, the third and fourth planes each intersect, in part, a fifth plane. Optionally, the first and second planes each intersect, in part, a sixth plane, where in one embodiment the fifth and sixth planes are the same plane.

The blade may be viewed in cross-section at any point between the cutting distal end and the non-cutting proximal end. The cross-section will include the two cutting edges of the knife, i.e., the cross-section is taken across the width of the knife blade and not along the length of the knife blade. The cross-section will have an upper profile (UP) defined, in part, by a baseline line segment that lies in the plane and terminates at the two cutting edges. The upper profile is also defined by a plurality of line segments that run coincident with the upper surface or periphery of the knife blade, where two of this plurality of line segments are joined, at one of their two ends, to the two ends of the baseline. The cross section will also have a lower profile (LP) which is defined by at least the baseline line segment, i.e., the same baseline line segment that also defines, in part, the upper profile. In other words, the baseline line segment defines the bottom of the upper profile while at the same time it defines the top of the lower profile.

The upper profile has a shape defined by the sum of the sides of the profile, and that shape is a concave polygon. The lower profile also has a shape, where that shape is selected from a concave polygon, a convex polygon, a straight line, and a half-ellipse. As used herein, the term "half-ellipse" denotes an ellipse which is bisected by a straight line, the straight line being the baseline line segment of the blade knife. When the lower profile is a concave polygon, the lower profile may have the same shape as the upper profile, i.e., the lower profile may be the mirror image of the upper profile where the baseline line segment forms the mirror boundary between the upper and lower profiles. Alternatively, the lower profile may have a differently shaped concave polygon compared to the concave polygon that defines the upper profile.

Turning first to the upper profile, in one embodiment, in the vicinity of the distal end of the knife blade, the blade has an upper profile that is in the shape of a concave polygon. As used herein, the term "polygon" has its usual meaning, and refers to a number of coplanar line segments, each connected end to end to form a closed shape. Likewise, the term "concave polygon" has its usual meaning, and refers to a polygon having one or more interior angles greater than 180°. The concave polygon will have n sides, where n is at least 4, and may be 5, or may be 6, or may be 7, or may be 8 or may be 9, or may be any two or more of the stated options. For example, the concave polygon may have 5 sides. As another example, the concave polygon may have 4 or 5 sides.

The upper profile includes a baseline, which is a straight line that runs directly between the two opposing cutting edges of the knife blade, as that blade is viewed in cross-section across the width of the blade. This baseline forms one line segment of the concave polygon that characterizes the upper profile. The baseline is connected, at its two ends, to two different line segments, referred to herein as the first and second line segments. The first line segment and the baseline join together at polygon vertex UB1 and form angle UaB1, while the second line segment and the baseline join together at polygon vertex UB2 and form angle UaB2.

When the concave polygon has 4 sides, i.e., n=4, one of those sides will be the baseline. In addition to the baseline, the concave polygon will have first and second line segments that are joined to the baseline, as described above. In addition, the first and second line segments will each join to a separate end of a third line segment. The first and third line segments join together at vertex U13, while the second and third line segments join together at vertex U23. Vertex U13 has an interior angle Ua13 that is greater than 180° but less than 330°. Angle Ua13 may be greater than 200°, or greater than 220°, or greater than 230°, or greater than 240°, or greater than 250°, where this angle may also, optionally or alternatively, be characterized in terms of a maximum size, and in various aspects is less than 320°, or is less than 300°, or is less than 280°, or is less than 270°, or is less than 260°. Any listed maximum angle may be combined with any listed minimum angle to provide a range of angles suitable to describe Ua13. For instance, and in specific aspects, Ua13 may be from 200-300°, or from 220-280°, or from 230-270°. Simultaneously, or alternatively, angles UaB1 and UaB2 may be defined in absolute or relative terms. For example, in one aspect, UaB2 is greater than UaB1.

FIG. 2A shows the line A-A' of the knife 10 illustrated in FIG. 1A at which a cross-section is taken, and that cross-section profile is shown in FIG. 2B. The profile shown in FIG. 2B is in the shape of a concave polygon with 5 sides, i.e., n=5. In this case, the two ends of the baseline B join to the first 1 and second 2 line segments at vertices UB1 and UB2 respectively, while the first 1 and second 2 line segments also join, at their opposite ends, to the ends of third 3 and fourth 4 line segments, respectively, at vertices U13 and U24, respectively, and the third 3 and fourth 4 line segments will join at their opposite ends to each other at vertex U34. Vertices UB1, UB2, U13, U24 and U34 may be defined as having inner angles UaB1, UaB2, Ua13, Ua24 and Ua34, respectively.

In one embodiment, each of angles UaB1 and UaB2 is independently less than 90°, less than 80°, less than 70°, less than 60°, less than 55°, less than 50°, less than 45°, less than 40°, less than 35°, less than 30°, less than 25°, less than 20°, less than 15°, less than 14°, less than 13°, less than 12°, less than 11°, or less than 10°, where these angles may also, optionally or alternatively, be characterized in terms of a minimum size, and in various aspects each of angles UaB1 and UaB2 is independently greater than 1°, greater than 2°, greater than 3°, greater than 4°, greater than 5°, greater than 6°, greater than 7°, greater than 8°, greater than 9°, greater than 10°, greater than 11°, greater than 12°, greater than 13°, greater than 14°, greater than 15°, greater than 20°, greater than 25°, greater than 30°, greater than 35°, greater than 40°, greater than 45°, greater than 50°, greater than 55°, greater than 60°, greater than 70°, or greater than 80°. Any listed maximum angle may be combined with any listed minimum angle to provide a range of permissible uB1 and uB2 angles. For instance, and in specific aspects, the angles UaB1 and UaB2 are each 5-15°. In one embodiment, each of angles uB1 and uB2 are approximately the same angle, in other words, are within 2° of each other.

In one embodiment, each of angles Ua13 and Ua24 is independently greater than 180°, greater than 190°, greater than 200°, greater than 210°, greater than 220°, greater than 230°, or greater than 240°, where these angles may also, optionally or alternatively, be characterized in terms of a maximum size, and in various aspects each of angles Ua13 and Ua24 is less than 330°, less than 320°, less than 310°, less than 300°, less than 290°, less than 280°, less than 270°, less than 260°, less than 250°, less than 240°, less than 230°, less than 220°, less than 210°, less than 200°. Any listed maximum angle may be combined with any listed minimum angle to provide a range of permissible Ua13 and Ua24 angles. For instance, and in specific aspects, the angles Ua13 and Ua24 are each 200-300°, or 220-280°. In one embodiment, each of angles Ua13 and Ua24 are approximately the same angle, in other words, are within 2° of each other.

In various embodiments when n=5, one or more of the following may describe the profile: the first and second line segments are approximately the same length, i.e., the length of the first line segment is within 5% of the length of the second line segment; the third and fourth line segments are approximately the same length, i.e., the third line segment has a length within 5% of the length of the fourth line segment; angles UaB1 and UaB2 are approximately equal, i.e., angle UaB1 is within 2° of angle UaB2; angles Ua13 and Ua24 are approximately equal, i.e., angle Ua13 is within 2° of angle Ua24. In one embodiment, the first and second line segments are approximately the same length, the third and fourth line segments are approximately the same length, angles UaB1 and UaB2 are approximately equal to one another, and angles Ua13 and Ua24 are approximately equal to one another. In one embodiment, the first and second line segments are approximately the same length, the third and fourth line segments are approximately the same length, angles UaB1 and UaB2 are approximately equal and are within the range of 5-15°, and angles Ua13 and Ua24 are approximately equal.

Turning now to the lower profile, in one embodiment the lower profile likewise is in the shape of a concave polygon. For example, in one embodiment, the lower profile is the mirror image of the upper profile. In this case, as illustrated in FIG. 1C, the top surface of the blade will look identical to the bottom surface of the blade. In other words, the lower profile can be described in the same terms as the upper profile. This embodiment, where the upper and lower profiles are the mirror image of one another, and both are concave polygons, may provide a knife blade referred to herein as a dual bevel blade. In another embodiment, the lower profile is no more than the baseline. In other words, the lower part of the knife is simply a flat plane. This embodiment, where the lower part of the knife lies in a single plane, while the upper profile has the shape of a concave polygon, provides a knife blade referred to herein as a single bevel blade.

In another embodiment, the lower profile may be a convex polygon, of 3, 4, 5, 6, 7 or 8 sides. This embodiment provides a knife blade referred to herein as a 1.5 bevel blade. For example, and in one embodiment, the lower profile may be a convex polygon where n=3, i.e., a polygon including the baseline and two additional sides, namely a first side and a second side. The first side joins to the baseline at vertex LB1 and forms an angle LaB1 with the baseline, while the second side joins to the baseline at vertex LB2 and forms an angle LaB2 with the baseline. In various aspects, the angles LaB1 and LaB2 are each independently less than 90°, less than 80°, less than 70°, less than 60°, less than 55°, less than 50°, less than 45°, less than 40°, less than 35°, less than 30°, less than 25°, less than 20°, less than 15°, where these angles may also, optionally or alternatively, be characterized in terms of a minimum size, and in various aspects each of angles LaB1 and LaB2 is independently greater than 5°, greater than 15°, greater than 20°, greater than 25°, greater than 30°, greater than 35°, greater than 40°, greater than 45°, greater than 50°, greater than 55°, greater than 60°, greater than 70°, or greater than 80°. Any listed maximum angle may be combined with any listed minimum angle to provide a range of permissible LaB1 and LaB2 angles. For instance, and in specific aspects, the angles LaB1 and LaB2 are each 5-10°. In one embodiment, each of angles LaB1 and LaB2 are approximately the same angle, in other words, are within 2° of each other. In one embodiment, LaB1, LaB2, UaB1 and UaB2 are approximately equal, and are each within the range of 5-15°.

The lower profile may alternatively be in the shape of a half-ellipse. As used herein, the term "half-ellipse" refers to an ellipse which has been intersected by a straight line, where the baseline line segment is that intersecting line. In such a case, the bottom of the knife is essentially curved. It is not planar, but when viewed in cross-section, it does not include vertices between straight line segments.

An upper profile in the shape of a concave polygon has been found to impart superior cutting ability to a knife blade that includes this profile, particularly as that blade is inserted into tissue. This particular knife blade geometry provides for wound creation with less force than is needed with prior art knives.

The knife blade as described herein, having an upper profile in the shape of a concave polygon, and a lower profile optionally in the shape of a concave polygon, a convex polygon, a straight line or a half-ellipse, may have alternative profiles at different places along the longitudinal axis of the knife or blade. For example, at an alternative location along the longitudinal axis, the upper profile (UP) may be in the form of a concave polygon which is non-identical to the form of the concave polygon present at a more distal end of the knife. In other words, the knife blade may, at two different locations (location 1, e.g., line A-A' in FIG. 2A, and location 2, e.g., line B-B' in FIG. 2A) along the longitudinal axis have two different profiles which are each described as a concave polygon. In this embodiment, the two different profiles will be referred to herein as upper profile 1 (UP1) which is a profile relatively close to the distal end of the knife blade, and upper profile 2 (UP2) which is a profile relatively far from the distal end of the knife blade. Similarly, at these two locations, there will be a lower profile (LP1) corresponding to but not necessarily identical to UP1, and a lower profile (LP2) corresponding to but not necessarily identical to UP2.

Exemplary upper and lower profiles of a knife blade of the present disclosure are illustrated by reference to FIGS. 1G to 1I as has been discussed previously. In these figures, the upper profile is identical to the lower profile. FIG. 1G shows a knife 10 having a distal end 20, a proximal handle end 45 and a point or tip 25. The distal end 20 of the knife is shown in expanded view in FIG. 1H and FIG. 1I.

FIG. 1H illustrates a blade 15 of a knife 10 of the present disclosure in expanded view, looking along the longitudinal axis of the knife towards the tip, or point, of the knife. FIG. 1H shows the knife tip 25 at the distal end of the knife, and the handle end 45 at the proximal end of the knife: in this view, it can be seen that the handle is round, however other suitable cross-sectional shapes, e.g., squares, pentagons, irregular shapes, etc., may be employed for the handle. FIG. 1H shows the cutting edges 30 and 35 which meet at point 25. FIG. 1H shows a knife of the present disclosure which is symmetrical around the longitudinal axis 40. In other words, the lower profile of the knife is identical to the upper profile of the knife, and the right and left hand sides of the knife are identical to one another.

FIG. 1I illustrates a blade 15 of a knife 10 of the present disclosure in expanded view, looking from the side of the knife at the proximal or cutting end of the blade. FIG. 1I shows the knife tip 25 at the distal end of the knife FIG. 1I also shows the cutting edge 35 of the blade. The cutting edge 35 is one of the sides of the plane 27, shown also in FIG. 1E. Plane 27 intersects with, and forms a common side with, plane 28, again also shown in FIG. 1E. Line 2728 from FIG. 1E can be seen located between planes 27 and 28. Line 2829 can be seen as one edge of plane 28, however the neighboring plane, plane 29, cannot be seen in this view. FIG. 1I shows a knife of the present disclosure which is symmetrical around the longitudinal axis 40. In other words, the lower profile of the knife is identical to the upper profile of the knife.

In one embodiment, as illustrated in FIG. 2A-C, UP1 is a concave polygon of other than 6 sides, e.g., a pentagon, while UP2 is a six-sided concave polygon, i.e., a polygon of n=6 or a hexagon. In this embodiment, at UP2 shown along lines B-B', the two ends of the baseline join to the first and second line segments at vertices UB1 and UB2 respectively, while the first and second line segments also join, at their opposite ends, to the ends of third and fourth line segments, respectively, at vertices U13 and U24, respectively, and the third and fourth line segments will join at their opposite ends to the ends of a fifth line segment at vertices U35 and U45, respectively. Vertices UB1, UB2, U13, U24, U35 and U45 may be defined as having inner angles UaB1, UaB2, Ua13, Ua24, Ua35 and Ua45, respectively.

In one embodiment, each of angles UaB1 and UaB2 of UP2 is independently less than 90°, less than 80°, less than 70°, less than 60°, less than 55°, less than 50°, less than 45°, less than 40°, less than 35°, less than 30°, less than 25°, less than 20°, less than 15°, where these angles may also, optionally or alternatively, be characterized in terms of a minimum size, and in various aspects each of angles UaB1 and UaB2 is independently greater than 5°, greater than 15°, greater than 20°, greater than 25°, greater than 30°, greater than 35°, greater than 40°, greater than 45°, greater than 50°, greater than 55°, greater than 60°, greater than 70°, or greater than 80°. Any listed maximum angle may be combined with any listed minimum angle to provide a range of permissible UaB1 and UaB2 angles. For instance, and in specific aspects, the angles UaB1 and UaB2 are each 5-15°. In one embodiment, each of angles uB1 and uB2 are approximately the same angle, in other words, are within 2° of each other.

In one embodiment, each of angles Ua13 and Ua24 of UP2 is independently greater than 180°, greater than 190°, greater than 200°, greater than 210°, greater than 220°, greater than 230°, or greater than 240°, where these angles may also, optionally or alternatively, be characterized in terms of a maximum size, and in various aspects each of angles Ua13 and Ua24 is less than 330°, less than 320°, less than 310°, less than 300°, less than 290°, less than 280°, less than 270°, less than 260°, less than 250°, less than 240°, less than 230°, less than 220°, less than 210°, less than 200°. Any listed maximum angle may be combined with any listed minimum angle to provide a range of permissible Ua13 and Ua24 angles. For instance, and in specific aspects, the angles Ua13 and Ua24 are each 200-300°, or 220-280°. In one embodiment, each of angles Ua13 and Ua24 are approximately the same angle, in other words, are within 2° of each other.

In various embodiments, one or more of the following may describe a relationship between the concave polygons of UP1 and UP2 where the concave polygon at UP1 is a pentagon and the concave polygon at UP2 is a hexagon: angle UaB1 at UP1 and angle UaB1 at UP2 are approximately the same, in other words, are within 2° of each other; angle UaB2 at UP1 and angle UaB2 at UP2 are approximately the same; angle Ua13 at UP1 and angle Ua13 at UP2 are approximately the same; angle Ua24 at UP1 and angle Ua24 at UP2 are approximately the same. In one embodiment, angle UaB1 at UP1 and angle UaB1 at UP2 are approximately the same and angle UaB2 at UP1 and angle UaB2 at UP2 are approximately the same and angle Ua13 at UP1 and angle Ua13 at UP2 are approximately the same and angle Ua24 at UP1 and angle Ua24 at UP2 are approximately the same. Optionally, LP1 is the mirror image of UP1 and LP2 is the mirror image of UP2. In an alternative embodiment, LP1 and LP2 are identical to one another.

As illustrated by the line C-C' in FIG. 2A, the knife blade 15 may have a cross-section at a distance proximal to the first cross section at line A-A' and at a distance proximal to the second cross section B-B'. This cross-section will likewise have an upper profile (UP3) and a lower profile (LP3), where those two profiles share a baseline line segment. In one embodiment, the upper profile of the third cross-section is in the form of a convex polygon. The convex polygon may have 3 sides, i.e., n=3, or 4 sides, or 5 sides, or 6 sides. FIG. 2D illustrates an embodiment where the convex polygon of the upper profile of the third cross section (UP3) is a convex polygon having four sides (sides B, 1, 2 and 3). In one embodiment, the angle between line segments B and 1, i.e., angle UaB1 of UP3, is the same as the corresponding angle UaB1 at the first and/or the second cross-sections, i.e., UP1 and/or UP2. Likewise, the angle between line segments B and 2, i.e., angle UaB2 of UP3, is the same as the corresponding angle UaB2 at the first and/or the second cross-sections, i.e., UP1 and/or UP2.

FIG. 3 illustrates embodiments of the knife 10 having a blade 15. The knife 10 will have a blade 15 and a handle 60. Preferably, the blade is symmetrical with respect to the longitudinal axis 40 of the knife 10. A cutting edge, for example cutting edge 30, may continue from distal cutting point 25 to a termination point at which the cutting edge 30 no longer functions as a cutting edge. In FIG. 3, this termination point is identified as ear 65 in regard to cutting edge 30, and ear 70 in regard to cutting edge 35. For ophthalmic surgical purposes, the blade 15 is fairly small. For example, the distance between ears 65 and 70 may be on the order 1-10 mm, or 1.5-8 mm, or 2-5 mm. Likewise, the distance between line 75 that links ears 65 and 70, and the distal cutting point 25, may be on the order of 2-5 mm, or 3-4 mm, or 3.5-4 mm. The size of the handle should be sufficient to be conveniently held by the health care provider that is using the knife. The knife 10 will typically have some region, shown as 95 in FIG. 3, which is intermediate the blade 15 and the handle 60, where this region 95 effectively functions to join together the blade 15 and the handle 60, and the position the blade 15 relative to the handle 60.

The knife blades disclosed herein may be prepared by taking a piece of stainless steel sire, and using a flat panel press to flatten a region of the wire. This flattened region may then be exposed to suitably shaped die in a punch press, to provide the desired shape of the blade. Some excess metal is often still attached to the knife blade after the punching process, but this excess metal may be removed by placing the knife blade into an acid bath. The acid dissolves the flashing leaving the desired blade. The acid treatment also reduces the size of the blade slightly from its original size. After the blade is the desired size and is free from any flashing, the blade may be coated with a lubricant, e.g., a silicone lubricant, and then cured in an oven.

A prior art knife blade is shown in FIG. 4A, where the blade 100 has a cutting edge 105 and a cutting edge 110 which meet at a distal cutting point 115. This blade 100 has an upper surface, typically flat, 120. The blade 100 is connected to a non-cutting intermediate region 400. Between the upper surface 120 and the cutting edge 105 there lies the bevel 125 of the blade 100. Likewise, between the upper surface 120 and the cutting edge 110 there lies the bevel 130 of the blade 100.

In comparison to such a prior art blade 100, in an embodiment of the present invention illustrated in FIG. 4B, there is provided one or more wedges that are inserted into the bevel of the blade 200. As shown in FIG. 4B, two wedges are illustrated, wedge 250 and wedge 255. The wedge 250 will have a length as measured by a direct line from its beginning at the distal tip 215 to its end as shown by location 260. The wedge will also have a maximum depth and a maximum width. The wedge may also be characterized in terms of the angle between the cutting edge 205 and a direct line drawn from the distal tip 215 and the end of the wedge 260. The wedge may also be characterized in terms of the angle formed when the walls of the wedge come together at the bottom of the wedge. A blade of the present invention may be characterized in terms of the number of wedges present in the blade, where exemplary numbers are 1, 2, 3 and 4. In one embodiment, the wedges are symmetrically placed relative to the longitudinal axis 40 of the blade. In one embodiment, there are two wedges, one on either side of the longitudinal axis of the blade and located in a symmetrical manner relative to the longitudinal axis. The presence of a wedge gives rise to additional cutting surfaces for the blade, resulting in a more effective blade, e.g., a blade that is easier for the health care provider to use. The presence of the wedge will be seen to provide a concave polygon shape to a cross-section that is taken across the wedge. The two sides of a wedge may be planar, or they may be non-planar, for example, they may be curved. The bevel of the blade may be in the form of a single plane, as shown in FIG. 4B, or it may be in the form of two planes which intersect. The cutting edge 205 may be linear, as illustrated in FIG. 4B, or it may be non-linear, e.g., curved.

When wedges are introduced into the bevel of a blade, the upper surface of the blade 220 may be modified to accommodate the wedge feature. For example, the upper surface 220 may be formed of two intersecting planes, where the intersection is in the vicinity of the proximal ends of two wedges, for example, along line G-G' shown in FIG. 4B. The upper surface 220 in the region distal to the line G-G' may not lie in the same plane as the upper surface 220 in the region proximal to the line G-G'. The plane defining the upper surface 220 which is distal to the line G-G' may be tilted slightly upward, i.e., the distal portion of the plane defining the upper surface 220 which is distal to the line G-G' may be further removed from the plane of the blade (i.e., the baseline line segment B) compared to the proximal portion of the plane defining the upper surface 220 which is distal to the line G-G'.

As stated initially, the blades and knives of the present disclosure have a traditional slit blade design running from the ears of the blade for some distance towards the point of the blade. In FIG. 4B, that distance is between a line 75 that runs through the ears 65 and 70, and the line G-G' which runs through the proximal ends of the inner cutting surfaces 250 and 255. However, near its point 215, the blades and knives of the present disclosure introduce a second bevel which adds strength to the tip region of the blade while introducing little additional thickness. Such a bevel is provided by each of the inner cutting surfaces 250 and 255. Accordingly, the blades and knives of the present disclosure can be made with a thinness, and accordingly provide an enhanced sharpness, over much of the cutting edge surface to a degree that, absent the second bevel, would provide a knife with unacceptably low rigidness near the tip. Stated another way, the blades and knives of the present disclosure incorporate a second cutting surface (each of 250 and 255 being a second cutting surface) in the region of the tip, where this second cutting surface adds mass and hence strength to this tip region. Viewed across the center axis 40, the blades and knives of the present disclosure have a single cutting surface 225 or 230 on either side of the blade extending from a cutting edge 205 or 210, respectively, where those cutting surfaces 225 or 230 extend along a cutting edge 205 and 210, respectively, from an ear 65 and 70, respectively, and for some distance (to the line G-G') from an ear. In addition, the blades and knives of the present disclosure have two or more, preferably two cutting surfaces 225+250 or 230+255 when viewed from a cutting edge 205 or 210 respectively towards the central axis 40, where each of those two cutting surfaces extend from the tip point 215 to the line G-G'.

In other words, the blades and knives of the present disclosure have an outer cutting surface 225 or 230 which runs from the point 215 for a distance reaching an ear 65 or 70, respectively, and also have an inner cutting surface 250 or 255 which runs from the point 215 for a distance that is less than the distance to an ear 65 or 70. In FIG. 4B, that distance which is less than the distance to an ear 65 or 70 is the distance between the point 215 and the line G-G' where line G-G' intersects axis 40. An outer cutting surface 225 or 230 is in the form a plane having a first angle with respect an imaginary plane that encompasses the two cutting edges 205 and 210 of the blade, and the inner cutting surface 250 or 255 is in the form of a plane having a second angle with respect to the imaginary plane that encompasses the two cutting edges 205 and 210, where the first and second angles are non-identical. An outer cutting surface 225 or 230 is contiguous with an adjacent cutting edge 205 or 210, respectively, between the tip 215 and an ear 65 or 70, respectively, while an inner cutting surface 250 or 255 is contiguous with the outer cutting surface 225 or 230, respectively, between the tip point 215 and a distance (the distance between tip point 215 and the line G-G' along axis 40 in FIG. 4B) which is less than the distance (from the tip point 215 to the line 75 along axis 40 in FIG. 4B) to the ear. The outer cutting surface 225 or 230 will therefore abut or adjoin the inner cutting surface 250 or 255, respectively, for a distance, and will abut or adjoin the center region 220 for a distance.

Accordingly, in one aspect, the present disclosure provides a knife blade comprising a cutting distal end, a non-cutting proximal end, two cutting edges disposed on either side of the cutting end, the two cutting edges disposed in an imaginary plane, each cutting edge running from a tip of the blade to an ear of the blade, an outer cutting surface contiguous with each cutting edge, each outer cutting surface adjoining an inner cutting surface, each inner cutting surface running from the tip of the blade in a proximal direction for a distance which is less than the distance to an ear of the blade, an outer cutting surface forming a first angle relative to the imaginary plane and an inner cutting surface forming a second angle relative to the imaginary plane, where the first and second angles are non-identical. In optional embodiments, any two or more of which may be combined, the present disclosure additionally provides that: the blade comprises two inner cutting surfaces, where the two inner cutting surfaces adjoin one another for a distance; an inner cutting surface adjoins one but not two outer cutting surfaces; an inner cutting surface is a plane having three sides; an outer cutting surface is a plane having four sides, one of the four sides being a cutting edge; the blade is symmetrical across a central axis running from the tip of blade to the proximal end of the blade, i.e., the right and left sides of the blade look the same; a top side of the blade and a bottom side of the blade meet at the cutting edges, where the top and bottom sides are identical. As mentioned above, each inner cutting surface runs from the tip of the blade in a proximal direction for a distance which is less than the distance to an ear of the blade, where this direction is measured along a central axis of the blade, and may be up to 80%, or 70%, or 60%, or 50%, or 40%, or 35%, or 30%, or 25%, or up to 20% of the distance from the tip of the blade to an imaginary line (see, e.g., 75 in FIG. 3) that bisects the two ears of the knife. In contrast, each outer cutting surface runs a distance which is at least 100% of the distance from the tip of the blade to a line that bisects the two ears of the knife.

Any of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A knife blade having a point at a cutting distal end, a non-cutting proximal end, two cutting edges disposed on either side of the cutting end, an upper blade surface having an upper periphery and a lower blade surface having a lower periphery, the two cutting edges each disposed in a single plane and extending from the point of the knife blade to an ear of the knife blade, where a first cutting edge extends to a first ear and a second cutting edge extends to a second ear, and the first and second ears are linked by a straight line, the knife blade comprising first, second, third and fourth planes that define, in part, the periphery of the blade, wherein a side of the first plane and a side of the second plane are each a cutting edge of the blade, and the cutting edges meet at the point of the blade, where the first and second planes have an identical number of sides selected from 3 and 4 to form a triangle or quadrangle shape, respectively, and the third and fourth planes have an identical number of sides selected from 3 and 4 to form a triangle or quadrangle shape, respectively, where the first and third planes have a common side which extends from the tip of the knife and does not extend as far as the line which links the ears of the knife, the second and fourth planes have a common side which extends from the point of the knife and does not extend as far as the line which links the ears of the knife, and the third and fourth planes have a common side.

2. The knife blade of claim 1 wherein the third and fourth planes have equal surface area.

3. The knife blade of claim 1 wherein the first and second planes have equal surface area.

4. The knife blade of claim 1 wherein the third and fourth planes each have a surface area smaller than either of the first and second planes.

5. The knife blade of claim 1 wherein the first and second planes each have exactly 3 sides, and the third and fourth planes each have exactly 3 sides.

6. The knife blade of claim 1 wherein the first and second planes each have exactly 4 sides, and the third and fourth planes each have exactly 4 sides.

7. The knife blade of claim 1 wherein the first and third planes have a common side which extends from the point of the knife for a distance of up to 80% of the distance from the point of the knife to the line which links the ears of the knife.

8. The knife blade of claim 1 wherein the first and third planes have a common side which extends from the point of the knife for a distance of up to 40% of the distance from the point of the knife to the line which links the ears of the knife.

9. The knife blade of claim 1 wherein the point of the knife blade and the straight line which links the first and second ears are separated by a distance of 2-5 mm.

10. The knife blade of claim 1 wherein the distance between the first and second ears is 1-10 mm.

* * * * *